(12) United States Patent
Mizokawa et al.

(10) Patent No.: US 8,785,527 B2
(45) Date of Patent: Jul. 22, 2014

(54) SYNTHETIC RESIN COMPOSITION AND AUTOMOTIVE INTERIOR/EXTERIOR MATERIAL COMPRISING THE SAME

(75) Inventors: Shigeo Mizokawa, Saitama (JP); Yoshinori Negishi, Saitama (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 12/921,740

(22) PCT Filed: Feb. 25, 2009

(86) PCT No.: PCT/JP2009/053341
§ 371 (c)(1),
(2), (4) Date: Sep. 9, 2010

(87) PCT Pub. No.: WO2009/113389
PCT Pub. Date: Sep. 17, 2009

(65) Prior Publication Data
US 2011/0028611 A1     Feb. 3, 2011

(30) Foreign Application Priority Data
Mar. 10, 2008  (JP) ................. 2008-059576

(51) Int. Cl.
| *C07D 211/94* | (2006.01) |
| *C08K 5/34* | (2006.01) |
| *C08K 5/3435* | (2006.01) |
| *C08K 5/3432* | (2006.01) |
| *C08K 5/36* | (2006.01) |
| *C08K 5/372* | (2006.01) |
| *C08K 5/00* | (2006.01) |

(52) U.S. Cl.
CPC ............ *C07D 211/94* (2013.01); *C08K 5/3435* (2013.01); *C08K 5/3432* (2013.01); *C08K 5/36* (2013.01); *C08K 5/372* (2013.01); *C08K 5/005* (2013.01)
USPC ......................................................... 524/99

(58) Field of Classification Search
CPC .. C07D 211/94; C08K 5/3435; C08K 5/3432; C08K 5/36; C08K 5/372; C08K 5/005; C08L 2666/02
USPC ......................................................... 524/99
See application file for complete search history.

(56) References Cited

U.S. PATENT DOCUMENTS

| 4,021,432 | A | 5/1977 | Holt et al. | |
| 4,046,737 | A | 9/1977 | Holt et al. | |
| 4,049,647 | A | 9/1977 | Holt et al. | |
| 4,576,734 | A | 3/1986 | Ishii et al. | |
| 4,619,958 | A | 10/1986 | Haruna et al. | |
| 2004/0122137 | A1* | 6/2004 | Haruna et al. | ................. 524/89 |
| 2009/0012238 | A1* | 1/2009 | Endoh et al. | ................. 525/240 |
| 2009/0111699 | A1* | 4/2009 | Negishi et al. | ............... 504/361 |

FOREIGN PATENT DOCUMENTS

| CN | 1926107 A | 3/2007 |
| EP | 1 731 508 A1 | 12/2006 |
| EP | 2 210 918 A1 | 7/2010 |
| JP | 46-42618 A | 12/1971 |
| JP | 48-65180 A | 9/1973 |
| JP | 59-62651 A | 4/1984 |
| JP | 60-197747 A | 10/1985 |
| JP | 1-113368 A | 5/1989 |
| JP | 2-166138 A | 6/1990 |
| JP | 2005-239839 | 9/2005 |
| JP | 2008-202005 A | 9/2008 |
| WO | WO 2005/082852 A1 | 9/2005 |
| WO | WO 2006/082830 A1 | 8/2006 |

OTHER PUBLICATIONS

International Search Report for PCT/JP2009/053341 mailed Jun. 9, 2009.

(Continued)

*Primary Examiner* — Angela C Scott
(74) *Attorney, Agent, or Firm* — Birch, Stewart, Kolasch & Birch, LLP

(57) ABSTRACT

Disclosed are a synthetic resin composition having more excellent weather resistance and an automotive interior/exterior material comprising the synthetic resin composition.
Specifically disclosed are a synthetic resin composition comprising, per 100 parts by mass of a synthetic resin, as Component (A) a hindered amine compound represented by the following general formula (I):

$$\left[ R-O-N \underset{H_3C}{\overset{H_3C}{\diagup}} \underset{CH_3}{\overset{CH_3}{\diagdown}} O-\overset{O}{\underset{\|}{C}}-O \right]_n R^1 \quad (I)$$

(wherein R represents an alkyl group having 1 to 30 carbon atoms or the like; and n represents an integer of 1 to 6) or the following general formula (II):

$$\left[ R-O-N \underset{H_3C}{\overset{H_3C}{\diagup}} \underset{CH_3}{\overset{CH_3}{\diagdown}} \underset{O}{\overset{O}{\diagdown}} \underset{A}{\overset{R^2}{\diagup}} -O \right]_n X \quad (II)$$

(wherein R represents an alkyl group having 1 to 30 carbon atoms or the like) in an amount of 0.01 to 20 parts by mass, and as Component (B) a sulfur-containing antioxidant in an amount of 0.01 to 20 parts by mass;
and an automotive interior/exterior material comprising the synthetic resin composition.

7 Claims, No Drawings

(56) References Cited

OTHER PUBLICATIONS

Chinese Office Action dated Mar. 6, 2012 for Chinese Application No. 200980108252.3 with English translation.

Extended European search report issued in European Patent No. 09718560.1 on May 6, 2013.
Indian Examination Report issued in Indian Patent Application No. 2075/mumnp/2010 on Apr. 21, 2014.

* cited by examiner

SYNTHETIC RESIN COMPOSITION AND AUTOMOTIVE INTERIOR/EXTERIOR MATERIAL COMPRISING THE SAME

TECHNICAL FIELD

The present invention relates to a synthetic resin composition and an automotive interior/exterior material comprising the same, more particularly, to a synthetic resin composition, whose weather resistance is highly improved, as well as an automotive interior/exterior material containing the same.

BACKGROUND ART

It has been known that a synthetic resin is not endurable for a long-term use, since it is degraded by the effects of heat and light, which causes discoloration and deterioration in mechanical strength. As a countermeasure, for the purpose of preventing from the degradation of the synthetic resin, stabilization by adding a hindered amine compound, an ultraviolet absorber, an antioxidant or the like is prevailing.

Particularly, the hindered amine compound is added to the synthetic resin in order to improve weather resistance. Various hindered amine compounds, in addition to the exemplified compounds disclosed in the following Patent Documents 1 to 6, have been proposed.

On the other hand, it has been known that a sulfur-containing antioxidant can be used to improve heat resistance. For example, a synthetic resin containing a phenolic compound and a sulfur-containing compound is disclosed in the following Patent Document 7.

Patent Document 1: Japanese Examined Patent Application Publication No. 46-42618
Patent Document 2: Japanese Unexamined Patent Application Publication No. 48-65180
Patent Document 3: Japanese Unexamined Patent Application Publication No. 59-62651
Patent Document 4: Japanese Unexamined Patent Application Publication No. 1-113368
Patent Document 5: Japanese Unexamined Patent Application Publication No. 2-166138
Patent Document 6: International Publication No. WO2005/082852
Patent Document 7: Japanese Unexamined Patent Application Publication No. 60-197747

DISCLOSURE OF THE INVENTION

Problems to be Solved by the Invention

However, recently, requirements of high stability and weather resistance for a synthetic resin have become severer in the field of automotive parts and the like, and a satisfactory composition has not been obtained from the use of the hindered amine compounds described in Patent Documents 1 to 6 and various conventional additives and from the combinations of them, and therefore there are needs for further improvement. Additionally, in a method of blending a sulfur-containing antioxidant like that described in Patent Document 7, a sulfur-containing antioxidant produces acidic substance in the process of stabilization, and therefore there is a problem that an antagonistic action occurs and the weather resistance deteriorates when a hindered amine compound is used together.

Under such circumstances, an object of the present invention is to provide a synthetic resin composition having more excellent weather resistance, and an automotive interior/exterior material using the same.

Means for Solving the Problems

The present inventors have intensively studied to meet the object, and have finally found that blending a certain hindered amine compound in combination with a sulfur-containing antioxidant to a resin can confer more excellent weather resistance, thereby completing the present invention.

That is, a synthetic resin composition according to the present invention comprises, per 100 parts by mass of a synthetic resin, as Component (A) a hindered amine compound represented by the following general formula (I):

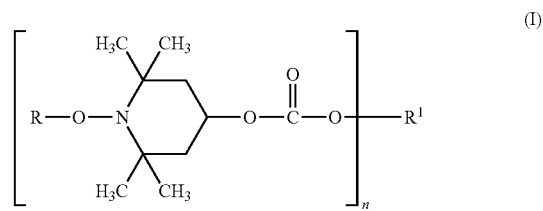

(wherein R represents an alkyl group having 1 to 30 carbon atoms, a hydroxyalkyl group having 1 to 30 carbon atoms, or an alkenyl group having 2 to 30 carbon atoms, n represents an integer of 1 to 6; when n=1, $R^1$ represents an alkyl group having 1 to 22 carbon atoms, an alkenyl group having 2 to 22 carbon atoms, or a group represented by the following general formula (III):

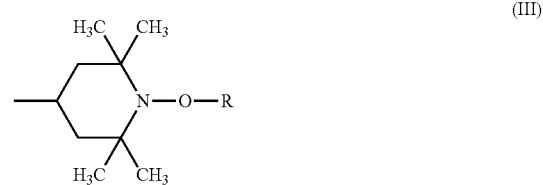

(wherein R represents an alkyl group having 1 to 30 carbon atoms, a hydroxyalkyl group having 1 to 30 carbon atoms, or an alkenyl group having 2 to 30 carbon atoms, and may be the same as or different from the R in the general formula (I)), and when n=2 to 6, $R^1$ represents n-valent organic group having 2 to 20 carbon atoms.)
or represented by the following general formula (II):

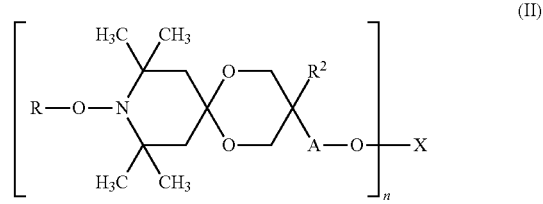

(wherein R represents an alkyl group having 1 to 30 carbon atoms, a hydroxyalkyl group having 1 to 30 carbon atoms, or an alkenyl group having 2 to 30 carbon atoms, $R^2$ represents a hydrogen atom, an alkyl group having 1 to 22 carbon atoms, or an alkenyl group having 2 to 22 carbon atoms, A represents a single bond, a linear or branched alkylene group having 1 to 12 carbon atoms, or a linear or branched alkylene group having 1 to 12 carbon atoms and an ether bond, n represents an integer of 2 to 6, X represents —C(=O)—, a linear or branched alkylene group having 4 to 40 carbon atoms and —C(=O)O— at terminal, a linear or branched alkylene group having 4 to 40 carbon atoms, —C(=O)O— at terminal and an ether bond in the middle, a linear or branched alkylene group having 4 to 40 carbon atoms and a carbonate ester bond, or an organic group having 6 to 30 carbon atoms and 3 to 6 groups of —O—C(=O)— at terminal) in an amount of 0.01 to 20 parts by mass;

and as Component (B) a sulfur-containing antioxidant in an amount of 0.01 to 20 parts by mass.

Additionally, in the synthetic resin composition according to the present invention, it is preferable that in the general formula (I), the n represents 1 and the $R^1$ is a group represented by the following general formula (III):

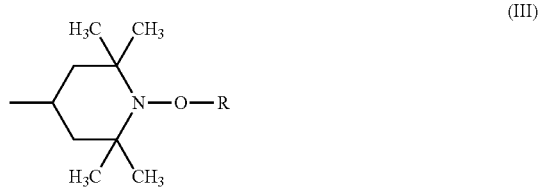

(III)

(wherein R represents an alkyl group having 10 to 22 carbon atoms). It is also preferable that in the general formula (I), the R represents an alkyl group having 4 to 22 carbon atoms, the n represents 2, and $R^1$ represents an alkylene group having 2 to 12 carbon atoms.

Further, in the synthetic resin composition according to the present invention, it is preferable that the sulfur-containing antioxidant contains a compound represented by the following general formula (IV):

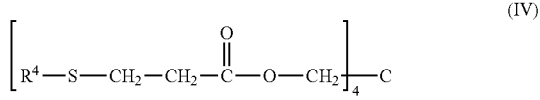

(IV)

(wherein $R^4$ represents an alkyl groups having 4 to 20 carbon atoms).

Furthermore, in the synthetic resin composition according to the present invention, it is preferable that the synthetic resin is a polyolefin resin and that the polyolefin resin is a polyethylene resin, a polypropylene resin, or an ethylene-propylene copolymer resin.

An automotive interior/exterior material according to the present invention is obtained by using the synthetic resin composition.

Effects of the Invention

The present invention can provide a synthetic resin composition having more excellent weather resistance, and an automotive interior/exterior material using the same.

BEST MODE FOR CARRYING OUT THE INVENTION

The present invention will be described in more details below.

Examples of a synthetic resin to be used according to the present invention include in the form of a thermoplastic resin: polyolefins or copolymers thereof, including α-olefin polymers, such as polypropylene, high density polyethylene, low density polyethylene, linear low density polyethylene, polybutene-1 and poly-4-methylpentene, ethylene-vinyl acetate copolymers and ethylene-propylene copolymers; halogen-containing resins, such as polyvinyl chloride, polyvinylidene chloride, chlorinated polyethylene, chlorinated polypropylene, polyvinylidene fluoride, chlorinated rubber, vinyl chloride-vinyl acetate copolymers, vinyl chloride-ethylene copolymers, vinyl chloride-vinylidene chloride copolymers, vinyl chloride-vinylidene chloride-vinyl acetate terpolymers, vinyl chloride-acrylic acid ester copolymers, vinyl chloride-maleic acid ester copolymers, and vinyl chloride-cyclohexyl maleimide copolymers; petroleum resins; coumarone resins; polystyrene; polyvinyl acetate; acrylic resins; copolymers of either or both of styrene and α-methylstyrene with other monomer(s), (e.g. maleic anhydride, phenylmaleimide, methyl methacrylate, butadiene, and acrylonitrile), such as AS resins, ABS resins, MBS resins, and heat resistant ABS resins; polymethyl methacrylate; polyvinyl alcohol; polyvinyl formal; polyvinyl butyral; linear polyesters, such as polyethylene terephthalate and polytetramethylene terephthalate; polyphenylene oxide; polyamides, such as polycaprolactam and polyhexamethylene adipamide; polycarbonate; branched polycarbonate; polyacetal; polyphenylene sulfide; polyurethane; and cellulosic resins; and mixtures thereof;

as well as in the form of a thermosetting resin: phenol resins, urea resins, melamine resins, epoxy resins, and unsaturated polyester resins. Furthermore, elastomers, such as isoprene rubbers, butadiene rubbers, acrylonitrile-butadiene copolymer rubbers, and styrene-butadiene copolymer rubbers, may be used. Among the afore-listed synthetic resins, polyolefin resins, such as polyethylene, polypropylene, and ethylene-propylene copolymer resins, are preferable for the synthetic resin composition according to the present invention.

The synthetic resins can be used irrespective of the specific gravity, average molecular weight, melt viscosity, monomer composition, insoluble rate in a solvent, existence or nonexistence or type of stereoregularity, shape and size at the completion of the polymerization, type of a catalyst used for the polymerization, existence or nonexistence or method of a residual catalyst deactivation or removal treatment, existence or nonexistence, type, or concentration of a residual metal or acid component in the resin originated from a catalyst.

Next, the Component (A) in the present invention will be described.

The hindered amine compound as the Component (A) in the present invention has a carbonate skeleton represented by the general formula (I) or (II).

Examples of the alkyl group having 1 to 30 carbon atoms represented by R in the general formulae (I) and (II) include linear or branched alkyl groups, such as methyl, ethyl, propyl, isopropyl, butyl, isobutyl, sec-butyl, tert-butyl, pentyl, sec-pentyl, tert-pentyl, hexyl, heptyl, octyl, isooctyl, 2-ethylhexyl, tert-octyl, nonyl, isononyl, decyl, undecyl, dodecyl, tridecyl, tetradecyl, pentadecyl, hexadecyl, heptadecyl, and octadecyl, and cycloalkyl groups, such as cyclohexyl groups.

In addition, examples of the hydroxyalkyl group having 1 to 30 carbon atoms represented by R in the general formulae (I) and (II) include 2-hydroxyethyl, 2-hydroxypropyl, 2-hydroxybutyl, and 2-hydroxy-2-methylpropyl.

Further, examples of the alkenyl group having 2 to 30 carbon atoms represented by R in the general formulae (I) and (II) include alkenyl groups that correspond to the above-exemplified alkyl groups, such as vinyl, allyl, butenyl, pentenyl, and oleyl.

The R's in n units may be the same as or different from each other per unit.

In the general formula (I), when n=1, $R^1$ represents an alkyl group having 1 to 22 carbon atoms, an alkenyl group having 2 to 22 carbon atoms, or a group represented by the general formula (III).

In the general formula (I), when n=1, examples of the alkyl group having 1 to 22 carbon atoms represented by the $R^1$ include methyl, ethyl, propyl, isopropyl, butyl, isobutyl, sec-butyl, tert-butyl, pentyl, sec-pentyl, tert-pentyl, hexyl, heptyl, octyl, isooctyl, 2-ethylhexyl, tert-octyl, nonyl, isononyl, decyl, undecyl, dodecyl, tridecyl, tetradecyl, pentadecyl, hexadecyl, heptadecyl, octadecyl, and behenyl.

In addition, in the general formula (I), when n=1, examples of the alkenyl group having 2 to 22 carbon atoms represented by the $R^1$ include alkenyl groups that correspond to the above-exemplified alkyl groups, such as vinyl, allyl, butenyl, pentenyl, and oleyl.

Further, in the general formula (I), when n=1 and the $R^1$ represents a group represented by the general formula (III), examples of the R in the general formula (III) are the same as those recited above for R in the general formula (I). The R in the general formula (III) may be the same as or different from the R in the general formula (I). Moreover, in the general formula (I), when n=1, it is preferable that the R is an alkyl group having 10 to 22 carbon atoms.

In the general formula (I), when n=2 to 6, examples of the n-valent organic group having 2 to 20 carbon atoms represented by the $R^1$ include residues of n-valent polyvalent hydroxy compound except for hydroxyl group.

Examples of the polyvalent hydroxy compound include ethylene glycol, propylene glycol, 1,3-propanediol, 1,2-butanediol, 1,3-butanediol, 1,4-butanediol, neopentyl glycol, 1,6-hexanediol, 1,3-cyclohexanediol, 1,4-cyclohexanediol, hydrogenated product of bisphenol A, hydrogenated product of bisphenol F, diethylene glycol, triethylene glycol, glycerine, trimethylolpropane, pentaerythritol, and dipentaerythritol.

In addition, in the general formula (I), it is preferable that the n is 2, the R is an alkyl group having 4 to 22 carbon atoms, and the $R^1$ is an alkylene group having 2 to 12 carbon atoms.

In the general formula (II), $R^2$ represents a hydrogen atom, an alkyl group having 1 to 22 carbon atoms, or an alkenyl group having 2 to 22 carbon atoms.

Examples of alkyl group having 1 to 22 carbon atoms represented by the $R^2$ include the groups satisfying the number of carbon atoms among those given above for the R.

In addition, in the general formula (II), examples of alkenyl group having 2 to 22 carbon atoms represented by the $R^2$ include the groups satisfying the number of carbon atoms among those given above for the R.

The $R^2$'s in n units may be the same as or different from each other per unit.

In the general formula (II), the A represents a single bond, a linear or branched alkylene group having 1 to 12 carbon atoms, or a linear or branched alkylene group having 1 to 12 carbon atoms and an ether bond.

In the general formula (II), examples of the linear or branched alkylene group having 1 to 12 carbon atoms represented by the A include methylene, 1,2-ethylene, 1,2-propylene, 1,3-propylene, tetramethylene, 1,2-butylene, 1,3-butylene, pentamethylene, 2,2-dimethyltrimethylene, hexamethylene, and octamethylene.

Additionally, in the general formula (II), examples of the linear or branched alkylene group having 1 to 12 carbon atoms and an ether bond represented by the A include

—$CH_2CH_2$—O—$CH_2CH_2$—,

—$CH_2CH(CH_3)$—O—$CH_2CH(CH_3)$—, and

—$CH_2CH_2$—O—$CH_2CH_2$—O—$CH_2CH_2$—.

In the general formula (II), the A's in n units (n is 2 to 6) may be the same as or different from each other per unit.

In the general formula (II), the X represents —C(=O)—, a linear or branched alkylene group having 4 to 40 carbon atoms and —C(=O)O— at terminal, a linear or branched alkylene group having 4 to 40 carbon atoms, —C(=O)O— at terminal, and an ether bond in the middle, a linear or branched alkylene group having 4 to 40 carbon atoms and a carbonate ester bond, or an organic group having 6 to 30 carbon atoms and 3 to 6 groups of —O—C(=O)— at terminal In the general formula (II), the alkylene group having 4 to 40 carbon atoms and —C(=O)—O— at terminal represented by the X include —C(=O)—O—$(CH_2)_p$—O—C(=O)—

(wherein p is a number of 2 to 40), and may have cycloalkylene group in the middle.

In the general formula (II), the linear or branched alkylene group having 4 to 40 carbon atoms, —C(=O)O— at terminal and an ether bond in the middle represented by the X include —C(=O)—O—$(CH_2)_q$—O—$(CH_2)$—O—C(=O)—

(wherein q is a number of 2 to 20).

In addition, in the general formula (II), the linear or branched alkylene group having 4 to 40 carbon atoms and a carbonate ester bond represented by the X include

—C(=O)—$R^3$—O—C(=O)—O—$R^3$—C(=O)—

(wherein $R^3$ represents an alkylene group having 2 to 18 carbon atoms).

Further, in the general formula (II), the organic group having 6 to 30 carbon atoms and 3 to 6 groups of —O—C(=O)— at terminal represented by the X include the following groups:

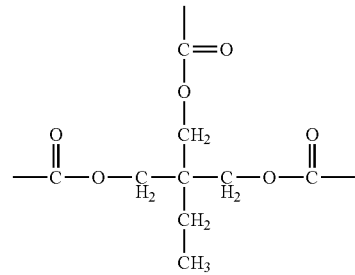

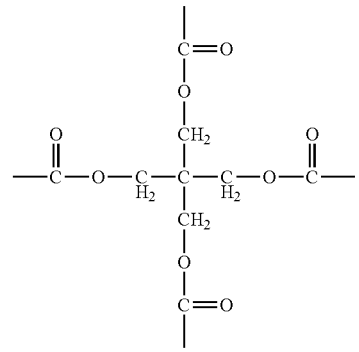

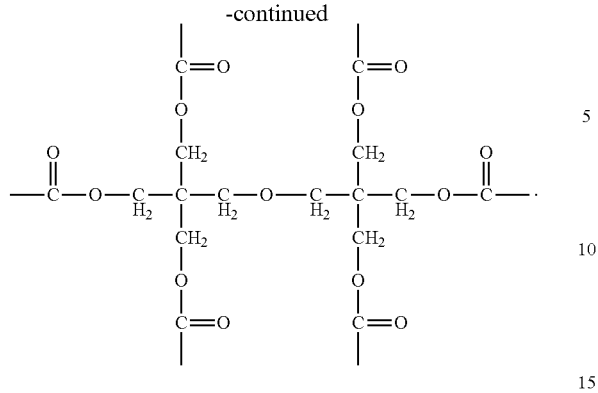
More particularly, examples of the compound represented by the general formulae (I) and (II) include the following compounds No. 1 to No. 7 and No. 8 to No. 13, respectively, provided that the present invention should not be construed to be limited by the following compounds in any manner.
Compound No.1
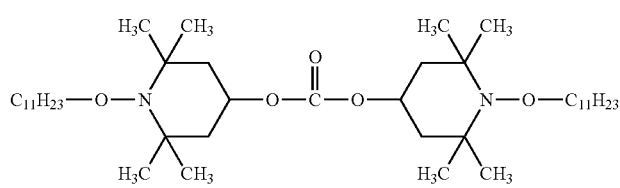
Compound No.2
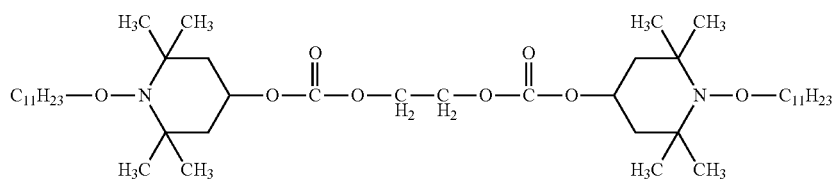
Compound No.3
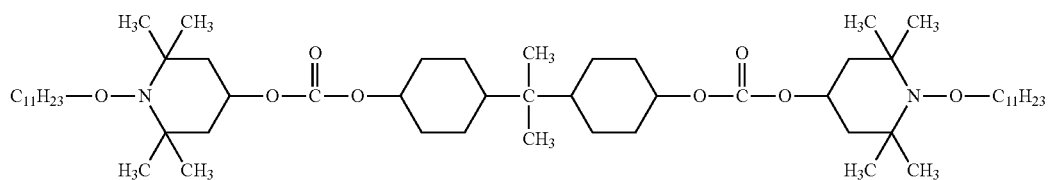
Compound No.4            Compound No.5
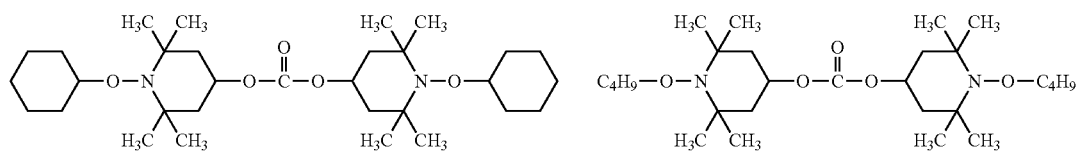
Compound No.6            Compound No.7
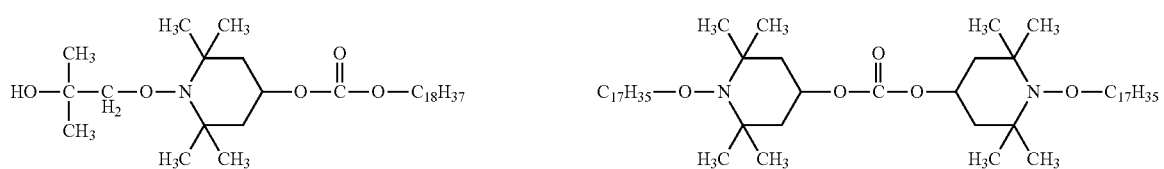

-continued

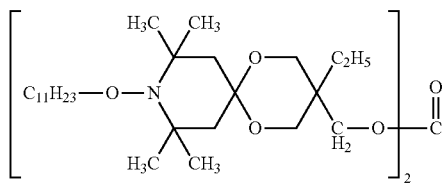
Compound No.8

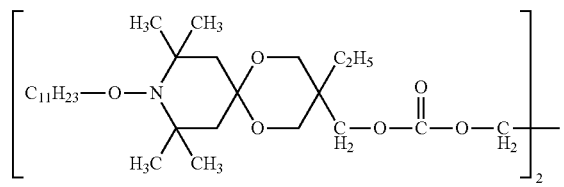
Compound No.9

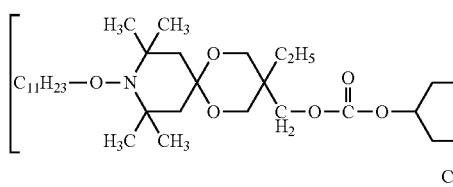
Compound No.10

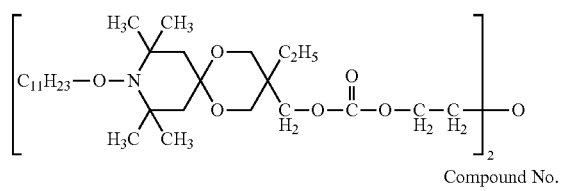
Compound No.11

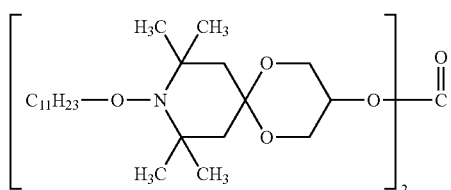
Compound No.12

Compound No.13

The synthetic process of the compounds represented by the general formula (I) is not particularly restricted, and the compounds can be synthesized by usual organic synthesis processes shown in Examples below. As the purification method, distillation, recrystallization, reprecipitation, a method in which a filtering material or absorption material is used, and the like, may appropriately be employed.

In addition, among the above-described specific examples, the Compound No. 1 is preferable in view of especially high imparting activity of weather resistance.

Next, the Component (B) in the present invention will be described.

The Component (B) in the present invention is a sulfur-containing antioxidant. As the sulfur-containing antioxidant, conventionally known sulfur-containing antioxidant may be used. Particularly, it is preferable to use a sulfur-containing compound represented by the general formula (IV) in view of imparting weather resistance.

In the general formula (IV), examples of the alkyl group having 4 to 20 carbon atoms represented by the $R^4$ include linear or branched alkyl groups, such as butyl, isobutyl, sec-butyl, tert-butyl, pentyl, sec-pentyl, tert-pentyl, hexyl, heptyl, octyl, isooctyl, 2-ethylhexyl, tert-octyl, nonyl, isononyl, decyl, undecyl, dodecyl, tridecyl, tetradecyl, pentadecyl, hexadecyl, heptadecyl, and octadecyl, and cycloalkyl groups, such as cyclohexyl groups.

Here, the $R^4$'s in 4 units may be the same as or different from each other per unit.

As a specific preferable example of a compound represented by the general formula (IV), the following Compound No. 14 is exemplified in view of imparting weather resistance.

Compound No. 14

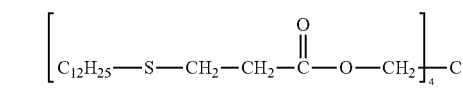

Additionally, a sulfur-containing compound represented by the following general formula (V):

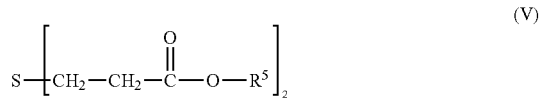
(V)

(wherein $R^5$ represents an alkyl group having 4 to 20 carbon atoms) is exemplified as other sulfur-containing antioxidant that may be used as the Component (B).

In the general formula (V), examples of the alkyl group having 4 to 20 carbon atoms represented by the $R^5$ include linear or branched alkyl groups, such as butyl, isobutyl, sec-butyl, tert-butyl, pentyl, sec-pentyl, tert-pentyl, hexyl, heptyl, octyl, isooctyl, 2-ethylhexyl, tert-octyl, nonyl, isononyl, decyl, undecyl, dodecyl, tridecyl, tetradecyl, pentadecyl, hexadecyl, heptadecyl, and octadecyl, and cycloalkyl groups, such as cyclohexyl groups.

Here, the $R^5$'s in 2 units may be the same as or different from each other per unit.

More particularly, examples of the compound represented by the general formula (V) include sulfur compounds of Compounds No. 15 to 18.

Compound No.15

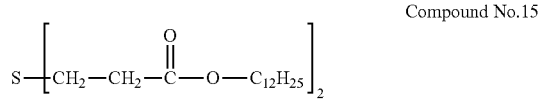

Compound No. 16

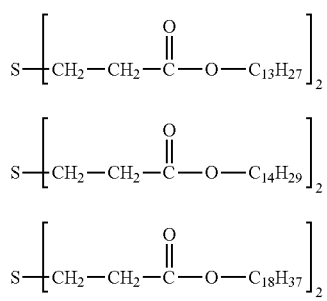

Furthermore, specific examples of the Component (B) include the following Compounds No. 19 to No. 23 which are sulfur compounds.

Compound No. 19

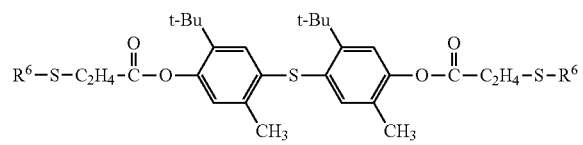

(wherein $R^6$ represents an alkyl group having 12 to 14 carbon atoms and denote the groups satisfying the number of carbon atom among those given above for the R.)

Compound No. 20

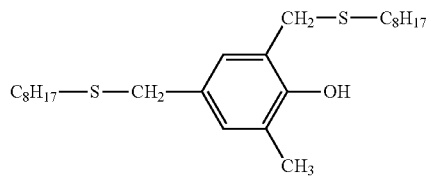

Compound No. 21

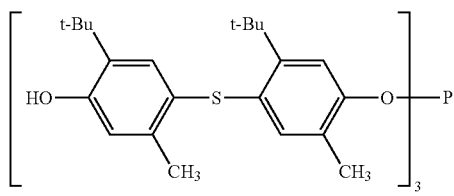

Compound No. 22

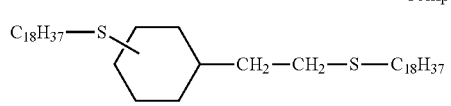

Compound No. 23

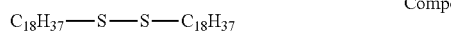

Next, the synthetic resin composition in the present invention will be described in more details below.

The synthetic resin composition of the present invention comprises, per 100 parts by mass of the synthetic resin, as Component (A) a hindered amine compound in an amount of 0.01 to 20 parts by mass, preferably 0.05 to 10 parts by mass, and more preferably 0.1 to 5 parts by mass, and as Component (B) a sulfur-containing antioxidant in an amount of 0.01 to 20 parts by mass, preferably 0.05 to 10 parts by mass, and more preferably 0.1 to 5 parts by mass. By containing the Components (A) and (B), the synthetic resin composition of the present invention exhibits excellent weather resistance.

In case the Component (A) is less than 0.01 part by mass, there is no sufficient weather resistance, and in case it is beyond 20 parts by mass, the appearance of the resin composition may be deteriorated by blooming and there is hardly an improvement of stabilizing activity.

Additionally, in case the Component (B) is less than 0.01 part by mass, there is no sufficient weather resistance, and in case it is beyond 20 parts by mass, the physical properties of the resin may be debased, or the appearance of the resin composition may be deteriorated by blooming.

Mass ratio of the Components (A) and (B) is preferably 1:0.05 to 1:5, more preferably 1:0.5 to 1:4, and most preferably 1:1 to 1:3. In case the Component (B) is less than 0.05 time to the Component (A), the improving activity of weather resistance may not be exhibited.

Besides the Components (A) and (B), the synthetic resin composition according to the present invention may contain, as necessary, other additives, such as a phenolic antioxidant, a phosphorus-containing antioxidant, an ultraviolet absorber, a hindered amine compound except the Component (A), a nucleating agent, a fire retardant, a fire retardant aid, a lubricant, a processing aid, a pigment, a filler, a plasticizer, a metallic soap, hydrotalcites, an antistatic agent, an antibacterial agent, and a compatibilizer.

Examples of the phenolic antioxidant include 2,6-di-tert-butyl-p-cresol, 2,6-diphenyl-4-octadecyloxyphenol, stearyl (3,5-di-tert-butyl-4-hydroxyphenyl)propionate, distearyl(3,5-di-tert-butyl-4-hydroxybenzyl)phosphonate, tridecyl 3,5 di.tert.butyl.4-hydroxybenzylthioacetate, thiodiethylene bis [(3,5-di-tert-butyl-4-hydroxyphenyl) propionate], 4,4'-thio-bis(6-tert-butyl-m-cresol), 2-octylthio-4,6-di(3,5-di-tert-butyl-4-hydroxyphenoxy)-s-triazine, 2,2'-methylene-bis(4-methyl-6-tert-butylphenol), bis[3,3-bis(4-hydroxy-3-tert-butylphenyl)butyric acid]glycol ester, 4,4'-butylidene-bis(2,6-di-tert-butylphenol), 4,4'-butylidene-bis(6-tert-butyl-3-methylphenol), 2,2'-ethylidene-bis(4,6-di-tert-butylphenol), 1,1,3-tris(2-methyl-4-hydroxy-5-tert-butylphenyl)butane, bis[2-tert-butyl-4-methyl-6-(2-hydroxy-3-tert-butyl-5-methyl benzyl)phenyl]terephthalate, 1,3,5-tris(2,6-dimethyl-3-hydroxy-4-tert-butylbenzyl)isocyanurate, 1,3,5-tris (3,5-di-tert-butyl-4-hydroxybenzyl)isocyanurate, 1,3,5-tris(3,5-di-tert-butyl-4-hydroxybenzyl)-2,4,6-trimethylbenzene, 1,3,5-tris[(3,5-di-tert-butyl-4-hydroxyphenyl)propionyl-oxyethyl] isocyanurate, tetrakis[methylene-3-(3',5'-di-tert-butyl-4'-hydroxyphenyl) propionate]methane, 2-tert-butyl-4-methyl-6-(2-acryloyloxy-3-tert-butyl-5-methylbenzyl)phenol, 3,9-bis[2-(3-tert-butyl-4-hydroxy-5-methylhydrocinnamoyloxy)-1,1-dimethylethyl]-2,4,8,10-tetraoxaspiro[5.5]undecane, triethylene glycol bis[β-(3-tert-butyl-4-hydroxy-5-methylphenyl)propionate, and tocopherol.

Examples of the phosphorus-containing antioxidant include triphenyl phosphite, tris(2,4-di-tert-butylphenyl) phosphite, tris(2,5-di-tert-butylphenyl)phosphite, tris(nonylphenyl)phosphite, tris(dinonylphenyl)phosphite, tris (mono- and di-nonylphenyl)phosphite, diphenyl acid phosphite, 2,2'-methylene bis(4,6-di-tert-butylphenyl)octyl phosphite, diphenyl decyl phosphite, diphenyl octyl phosphite, di(nonylphenyl)pentaerythritol diphosphite, phenyl-diisodecyl phosphite, tributyl phosphite, tris(2-ethylhexyl) phosphite, tridecyl phosphite, trilauryl phosphite, dibutyl acid phosphite, dilauryl acid phosphite, trilauryl trithiophosphite, bis(neopentyl glycol)1,4-cyclohexane dimethyl diphosphite, bis(2,4-di-tert-butylphenyl)pentaerythritol diphosphite, bis(2,5-di-tert-butylphenyl)pentaerythritol diphosphite, bis(2,6-di-tert-butyl-4-methylphenyl)pentaerythritol diphosphite, bis(2,4-dicumylphenyl)pentaerythritol diphosphite, distearyl pentaerythritol diphosphite, tetra (C12-C15 mixed alkyl)-4,4'-isopropylidene diphenyl phosphite, bis[2,2'-methylenebis(4,6-diamylphenyl)]isopropylidene diphenyl phosphite, tetra tridecyl 4,4'-butylidenebis(2-tert-butyl-5-methylphenol)diphosphite, hexa(tridecyl)1,1,3-tris(2-methyl-5-tert-butyl-4-hydroxyphenyl)butane.triphosphite, tetrakis(2,4-di-tert-butylphenyl) biphenylene diphosphonite, tris(2-[(2,4,7,9-tetrakis-tert-butyldibenzo[d,f][1,3,2]dioxaphosphepin-6-yl)oxy]ethyl) amine, 2-(1,1-dimethylethyl)-6-methyl-4-[3-[[2,4,8,10-tetrakis(1,1-dimethylethyl)dibenzo[d,f][1,3,2]dioxaphosphepin-6-yl]oxy]propyl]phenol, 9,10-dihydro-9-oxa-10-phosphaphenanthrene-10-oxide, and 2-butyl-2-ethylpropanediol 2,4,6-tri-tert-butylphenol monophosphite.

Examples of the ultraviolet absorber include 2-hydroxy benzophenones, such as 2,4-dihydroxy benzophenone, 2-hydroxy-4-methoxy benzophenone, 2-hydroxy-4-octoxy benzophenone, and 5,5'-methylene bis(2-hydroxy-4-methoxy benzophenone); 2-(2'-hydroxyphenyl)benzotriazoles, such as 2-(2'-hydroxy-5'-methylphenyl)benzotriazole, 2-(2'-hydroxy-3',5'-di-tert-butylphenyl)-5-chlorobenzotriazole, 2-(2'-hydroxy-3'-tert-butyl-5'-methylphenyl)-5-chlorobenzotriazole, 2-(2'-hydroxy-5'-tert-octylphenyl)benzotriazole, 2-(2'-hydroxy-3',5'-dicumylphenyl)benzotriazole, and 2-(2'-hydroxy-3'-tert-butyl-5'-carboxyphenyl)benzotriazole; benzoates, such as phenyl salicylate, resorcinol monobenzoate, 2,4-di-tert-butylphenyl-3,5-di-tert-butyl-4-hydroxybenzoate, 2,4-di-tert-amylphenyl-3,5-di-tert-butyl-4-hydroxybenzoate, and hexadecyl-3,5-di-tert-butyl-4-hydroxybenzoate; substituted oxanilides, such as 2-ethyl-2'-ethoxyoxanilide, and 2-ethoxy-4'-dodecyloxanilide; cyanoacrylates, such as ethyl-α-cyano-β,β-diphenyl acrylate and methyl-2-cyano-3-methyl-3-(p-methoxyphenyl)acrylate; triaryltriazines, such as 2-(2-hydroxy-4-octoxyphenyl)-4,6-bis(2,4-di-tert-butylphenyl)-s-triazine, 2-(2-hydroxy-4-methoxyphenyl)-4,6-diphenyl-s-triazine, and 2-(2-hydroxy-4-propoxy-5-methylphenyl)-4,6-bis(2,4-di-tert-butylphenyl)-s-triazine.

Examples of another hindered amine compound include 2,2,6,6-tetramethyl-4-piperidyl-1-oxy, 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl)sebacate, bis(1,2,2,6,6-pentamethyl-4-piperidyl)sebacate, tetrakis(2,2,6,6-tetramethyl-4-piperidyl) butanetetracarboxylate, tetrakis(1,2,2,6,6-pentamethyl-4-piperidyl butanetetracarboxylate, bis(2,2,6,6-tetramethyl-4-piperidyl)di(tridecyl)-1,2,3,4-butanetetracarboxylate, bis(1,2,2,6,6-pentamethyl-4-piperidyl) di(tridecyl)-1,2,3,4-butanetetracarboxylate, bis(1,2,2,6,6-pentamethyl-4-piperidyl)-2-butyl-2-(3,5-di-tert-butyl-4-hydroxybenzyl) malonate, a 1-(2-hydroxyethyl)-2,2,6,6-tetramethyl-4-piperidinol/diethyl succinate polycondensate, a 1,6-bis(2,2,6,6-tetramethyl-4-piperidylamino) hexane/dibromoethane polycondensate, a 1,6-bis(2,2,6,6-tetramethyl-4-piperidylamino) hexane/2,4-dichloro-6-morpholino-s-triazine polycondensate, a 1,6-bis(2,2,6,6-tetramethyl-4-piperidylamino)hexane/2,4-dichloro-6-tert-octylamino-s-triazine polycondensate, 1,5,8,12-tetrakis[2,4-bis(N-butyl-N-(2,2,6,6-tetramethyl-4-piperidyl)amino)-s-triazin-6-yl]-1,5,8,12-tetraazadodecane, 1,5,8,12-tetrakis[2,4-bis(N-butyl-N-(1,2,2,6,6-pentamethyl-4-piperidyl)amino)-s-triazin-6-yl]-1,5,8,12-tetraazadodecane, 1,6,11-tris[2,4-bis(N-butyl-N-(2,2,6,6-tetramethyl-4-piperidyl)amino)-s-triazin-6-ylaminoundecane, and 1,6,11-tris[2,4-bis(N-butyl-N-(1,2,2,6,6-pentamethyl-4-piperidyl)amino)-s-triazine-6-ylaminoundecane.

Examples of the nucleating agent include metal salts of an aromatic carboxylic acid, such as aluminum p-tert-butyl benzoate, and sodium benzoate; metal salts of an acidic phosphate ester, such as sodium bis(2,4-di-tert-butylphenyl)phosphate, lithium bis(2,4-di-tert-butylphenyl)phosphate, and sodium-2,2'-methylene-bis(4,6-di-tert-butylphenyl)phosphate; and polyhydric alcohol derivatives, such as dibenzylidene sorbitol, and bis(methylbenzylidene)sorbitol.

Examples of the fire retardant include halogen type fire retardants, such as tetrabromobisphenol A, and decabromodiphenyl ether; phosphorus type fire retardants based on inorganic phosphorus compounds, such as red phosphorus and melamine phosphate, and phosphoric ester compounds, such as triphenyl phosphate, a phenol/resorcinol/phosphoric acid condensate, and a bisphenol A/2,6-xylenol/phosphoric acid condensate; inorganic fire retardants, such as magnesium hydroxide, and aluminum hydroxide; and nitrogen-containing compounds, such as melamine cyanurate. The fire retardant should preferably be used in combination with a fire retardant aid, such as antimony oxide, or a drip-preventing agent, such as a fluorine-contained resin, and a silicone resin.

The pigment may be organic as well as inorganic, and examples thereof include white pigments, such as titanium oxide, and zinc sulfide; black pigments, such as carbon black; green pigments, such as chromium oxide, chrome green, zinc green, chlorinated copper phthalocyanine green, phthalocyanine green, naphthol green, and malachite green lake; blue pigments, such as ultramarine, iron blue, copper phthalocyanine blue, cobalt blue, phthalocyanine blue, fast sky blue, and indanthrene blue; red pigments, such as red lead, red iron oxide, basic zinc chromate, chrome vermilion, cadmium red, rose red, brilliant carmine, brilliant scarlet, quinacridone red, lithol red, vermilion, thioindigo red, and mingamiya red; and yellow pigments, such as chrome yellow, zinc yellow, yellow iron oxide, titan yellow, fast yellow, hansa yellow, auramine lake, benzidine yellow, and indanthrene yellow.

As the fillers are used glass fibers, talc, silica, calcium carbonate, etc. The surfaces of the fillers are preferably treated by a titanium-based or silane-based surface treatment agent to improve compatibility with resin.

As the metallic soap, are used salts between a metal, such as magnesium, calcium, aluminum, and zinc, and a saturated or unsaturated fatty acid, such as lauric acid, myristic acid, palmitic acid, stearic acid, behenic acid, and oleic acid. The soap can be used irrespective of the water content, melting point, particle size, composition of the fatty acids, selection of the production process between a metathetical process by a reaction of an alkali metal salt of a fatty acid with a metal oxide or hydroxide, and a direct process by a neutralization reaction of a fatty acid with a metal oxide or hydroxide in the presence or absence of a solvent, or whether either of the fatty acid or the metal is in excess.

As the hydrotalcites, both natural products and synthetic products can be used, and products modified by an alkali metal such as lithium can be also used. Especially, the product having a composition represented by the following general formula (VI), $$Zn_xMg_yAl_2(OH)_2(x+y+2)CO_3 \cdot nH_2O \qquad (VI)$$

(wherein x is 0 to 3, y is 1 to 6, x+y is 4 to 6, and n is 0 to 10) is preferable. The product can be used irrespective of the existence or nonexistence of crystal water or surface treatment. Although there is no particular restriction on the particle size, smaller size is preferable insofar as the properties of the hydrotalcite should not be lost. If the particle size is large, dispersibility becomes inadequate to decrease stabilizing activity, and the physical properties of a resulted product resin composition, such as mechanical strengths and transparency, will be compromised.

Examples of the lubricant include fatty acid amides, such as laurylamide, myristylamide, stearylamide and behenylamide; ethylene-bis-stearylamide; polyethylene wax; metal soaps, such as calcium stearate and magnesium stearate; and phosphoric acid ester metal salts, such as magnesium distearylphosphate and magnesium stearylphosphate.

For the respective ingredients, the contents and qualities thereof are selected appropriately in accordance with the resin types, process conditions and end uses.

Addition of the Components (A) and (B) and the other ingredients above into a resin may be carried out according to a conventional process, such as a process in which each ingredient is mixed independently into the resin by, for example, a Henschel mixer and supplied to a processing machine; a process in which ingredients other than the resin are mixed preliminarily in a given combination, formed into powder or granule and added to the resin; a process in which master pellets containing high concentration ingredients in a resin are added to the resin; and a process in which ingredients are fed to the resin through a feeding port different from the port for the resin using an extruder having a plurality of feeding ports.

There is no particular restriction on a processing process for the synthetic resin composition according to the present invention, and an appropriate conventional process is selected depending on a resin to be used, existence of fillers, etc. More particularly, the synthetic resin composition according to the present invention can be molded by a conventional process, such as extrusion molding, injection molding, compression molding, and laminate molding.

Although there is no particular restriction on the use of the synthetic resin composition according to the present invention, it can be used for general interior/exterior materials, preferably for interior/exterior materials of transport vehicle, and further preferably for the use exposed to outdoor radiation, such as automotive interior/exterior materials to be subjected to severe environments. Examples of automotive interior/exterior materials include exterior materials for a bumper, a spoiler, a side visor, a cowl vent grille, a radiator grille, a side molding and a rear panel garnish, and interior materials for an instrument panel, a ceiling, a door, a seat and a luggage room.

EXAMPLES

The present invention will be described in more detail by way of examples thereof. However, the present invention should not be construed to be limited by the examples.

Synthesis Example 1

Synthesis of Compound No. 1

First, 17.0 g (98.1 mmol) of 4-hydroxy-1-oxy-2,2,6,6-tetramethyl piperidine was dissolved in 40.0 g of chlorobenzene and a solution prepared by dissolving 31.3 g (78.5 mmol) of dilauroyl peroxide in 125 g of chlorobenzene at 70° C. was added thereto dropwise in 3 hours. A reaction in the mixture proceeded at the same temperature for 6 hours. The obtained reaction solution was analyzed by gas chromatography and disappearance of raw materials was confirmed. The obtained reaction solution was a mixture of 4-hydroxy-1-undecanoxy-2,2,6,6-tetramethylpiperidine, 1-undecanoxy-2,2,6,6-tetramethylpiperidine-4-one, lauric acid, and solvent. To the reaction solution, 50 g of hexane was added. The solution was washed by adding 53.9 g (98 mmol) of 7.3% sodium hydroxide solution and 25 g of methanol, and further washed twice with 30 g of water to remove lauric acid. The solution was dried with anhydrous magnesium sulfate, filtered to remove the magnesium sulfate, evaporated under reduced pressure to remove solvent by an evaporator, and then a condensation was obtained. To the condensation, 70 ml of ethanol was added, and then 20 ml of ethanol solution containing 0.57 g (15 mmol) of sodium borohydride was added dropwise in 20 minutes. Moreover, a reaction in the solution proceeded for 1 hour and disappearance of 1-undecanoxy-2,2,6,6-tetramethylpiperidine-4-one was confirmed. The solution was evaporated under reduced pressure to remove solvent, 50 ml of toluene was added thereto, and washing with 30 ml of water was repeated five times. Then, dehydrating under reflux and reduced pressure and removing solvent under reduced pressure were performed at 40° C., and 23.0 g of 4-hydroxy-1-undecanoxy-2,2,6,6-tetramethylpiperidine (68.8% yield) was obtained as colorless liquid, of which purity is 96.1% based on area ratio by gas chromatography.

In 100 ml of mineral spirit, 12.0 g (35.17 mmol) of the obtained 4-hydroxy-1-undecanoxy-2,2,6,6-tetramethylpiperidine with 96.1% purity, 4.19 g (19.34 mmol) of diphenyl carbonate, and 0.6 g of potassium carbonate were dispersed, and a reaction therein proceeded at 170 to 180° C. for 8 hours to remove phenol. The mixture was cooled to 40° C. and washed with 30 ml of water three times. The mixture was dehydrated under reflux and reduced pressure at 60° C., removed solvent under reduced pressure by an evaporator, and then a condensation was obtained. The condensation was purified by silica gel chromatography (developing solution: toluene). Then, bis(1-undecanoxy-2,2,6,6-tetramethylpiperidine-4-yl) carbonate (55.5% yield) (Compound No. 1) was obtained as colorless liquid, of which purity is 99.9% based on area ratio by gas chromatography.

Analysis results of the obtained Compound No. 1 is described below.

IR Spectrum 2800 to 3050 $cm^{-1}$, 1740 $cm^{-1}$, 1450 $cm^{-1}$, 1380 $cm^{-1}$, 1360 $cm^{-1}$, 1310 $cm^{-1}$, 1270 $cm^{-1}$, 1240 $cm^{-1}$, 1190 $cm^{-1}$, 1000 $cm^{-1}$ $^1$H-NMR spectrum (H: is measured value of proton number and value in [ ] is calculated value)

δ 0.75 to 2.05 (H: of $CH_3$ and C—$CH_2$—C is 72.8 [74])

δ 3.55 to 3.85 (H: of $CH_2$—O is 4.2 [4])

δ 4.60 to 5.10 (H: of CH-0 is 2.0 [2])

Examples 1 to 3 and Comparative Examples 1 to 6

85 parts by mass of an ethylene-propylene copolymer resin (MFR=25, density=0.90 $g/cm^3$, flexural modulus=1,700 MPa), 15 parts by mass of talc, 3.0 parts by mass of a gray pigment, 0.1 part by mass of tetrakis[methylene-3-(3',5'-di-tert-butyl-4'-hydroxyphenyl) propionate)]methane, 0.1 part by mass of tris(2,4-di-tert-butylphenyl) phosphite, 0.1 part by mass of calcium stearate, and a hindered amine compound and a sulfur-containing antioxidant as set forth in the following Tables 1 and 2 (the unit of amount in Table 1 is part by mass) were extruded at 230° C. to pellets. The yielded pellets were injection-molded at 230° C. to 2 mm-thick test pieces.

In composition described in Tables 1 and 2, the Compound No. 1 obtained by the method described in the Synthesis Example and the above Compound No. 14 (ADKSTAB AO-412S, produced by ADEKA CORPORATION) were used as the Component (A) and (B), respectively. In addition, the following Comparative Compounds-1 and -2 were used to compare with the Component (A) which is a hindered amine compound.

Comparative Compound-1

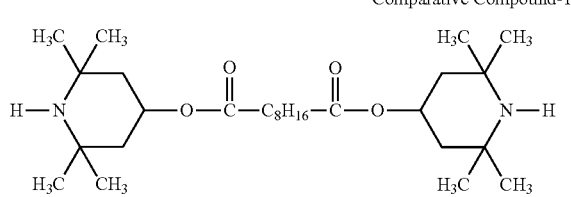

TABLE 1

|  |  |  | Examples | | |
|---|---|---|---|---|---|
|  |  |  | 1 | 2 | 3 |
| Component (A) | Compound No. 1 |  | 0.2 | 0.15 | 0.1 |
|  | Comparative Compound-1 |  | — | — | — |
|  | Comparative Compound-2 |  | — | — | — |
| Component (B) | Compound No. 14 |  | 0.3 | 0.25 | 0.1 |
| Evaluation of weather resistance | Time to cracking (hr) |  | 1560 | 1440 | 1200 |
|  | Residual rate of gloss (%) | 480 hr | 100 | 100 | 100 |
|  |  | 720 hr | 100 | 100 | 100 |
|  |  | 1080 hr | 96 | 88 | 65 |
|  | Color difference ($\Delta E$) | 480 hr | 0.38 | 0.52 | 0.55 |
|  |  | 720 hr | 0.62 | 0.62 | 1.56 |
|  |  | 1080 hr | 1.23 | 1.53 | 1.77 |

TABLE 2

|  |  |  | Comparative Examples | | | | | | |
|---|---|---|---|---|---|---|---|---|---|
|  |  |  | 1 | 2 | 3 | 4 | 5 | 6 | 7 |
| Component (A) | Compound No. 1 |  | 0.2 | — | — | — | — | 0.5 | — |
|  | Comparative Compound-1 |  | — | 0.2 | — | 0.2 | — | — | — |
|  | Comparative Compound-2 |  | — | — | 0.2 | — | 0.2 | — | — |
| Component (B) | Compound No. 14 |  | — | — | — | 0.3 | 0.3 | — | 0.5 |
| Evaluation of weather resistance | Time to cracking (hr) |  | 840 | 1080 | 1080 | 840 | 1080 | 1080 | 360 |
|  | Residual rate of gloss (%) | 480 hr | 57 | 91 | 96 | 86 | 100 | 72 | — |
|  |  | 720 hr | 29 | 61 | 74 | 36 | 97 | 38 | — |
|  |  | 1080 hr | — | 31 | 42 | — | 25 | — | — |
|  | Color difference ($\Delta E$) | 480 hr | 1.81 | 0.74 | 0.77 | 0.98 | 0.65 | 1.72 | — |
|  |  | 720 hr | 2.88 | 2.12 | 0.90 | 2.46 | 1.86 | 2.66 | — |
|  |  | 1080 hr | — | 2.28 | 2.28 | — | 2.83 | — | — |

-continued

Comparative Compound-2

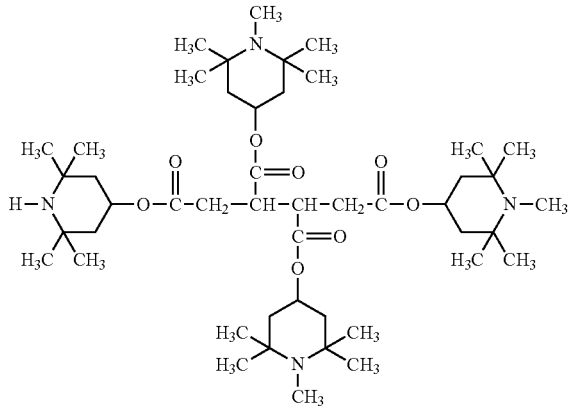

<Evaluation>

The weather resistance of a test piece was evaluated by means of the time to cracking (hr), the residual rate of gloss (%) and the color difference ($\Delta E$) by a xenon irradiation test (conditions: UV irradiation intensity 0.55 W/m², wavelength 340 nm, black panel temperature 89° C., and with a quartz filter). The gloss (unitless) was measured by Gloss Meter, Model TC-108D (produced by Tokyo Denshoku CO., LTD.). The obtained results are shown in the following Tables 1 and 2.

It is obvious from the results shown in Tables 1 and 2, that the synthetic resin composition of the present invention exhibits excellent weather resistance, due to the addition of a hindered amine compound of Component (A) and a sulfur-containing antioxidant of Component (B), indicating a noticeable effect thereof. It is further clear that such noticeable effect can be attained only by a combination of the hindered amine compound of the Component (A) according to the present invention and a sulfur-containing antioxidant of the Component (B), while there is no such improvement of weather resistance for a combination of a hindered amine compound which is not the Component (A) according to the present invention and the sulfur-containing antioxidant.

The invention claimed is:

1. An automotive interior/exterior material, which is obtained by using a synthetic resin composition comprising, per 100 parts by mass of a synthetic resin, as Component (A) a hindered amine compound represented by the following general formula (I):

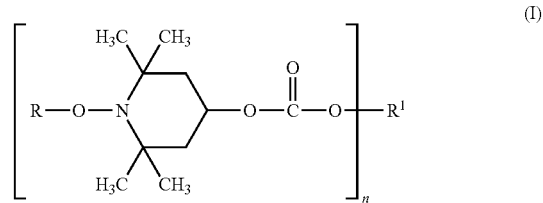

wherein R represents an alkyl group having 10 to 22 carbon atoms, n represents an integer of 1, $R^1$ represents a group represented by the following general formula (III):

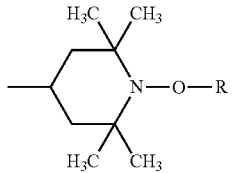

(III)

wherein R represents an alkyl group having 10 to 22 carbon atoms, and may be the same as or different from the R in the general formula (I) in an amount of 0.1 to 5 parts by mass; and as Component (B) a sulfur-containing antioxidant represented by the general formula (IV) in an amount of 0.1 to 5 parts by mass,

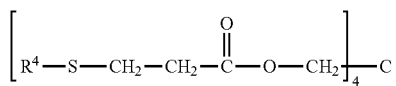

(IV)

wherein $R^4$ represents an alkyl groups having 10 to 15 carbon atoms, and wherein the mass ratio between (A) and (B) is 1:1 to 1:3.

2. The automotive interior/exterior material according to claim 1, wherein the synthetic resin is a polyolefin resin.

3. The automotive interior/exterior material according to claim 2, wherein the polyolefin resin is a polyethylene resin, a polypropylene resin, or an ethylene-propylene copolymer resin.

4. The automotive interior/exterior material according to claim 1, wherein the Component (A) a hindered amine compound is a compound represented by the following formula:

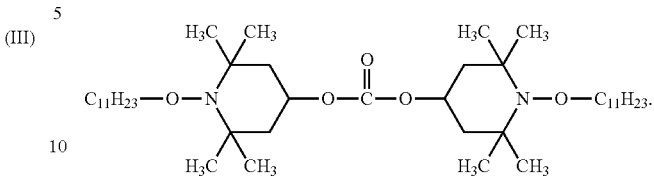

5. The automotive interior/exterior material according to claim 4, wherein the Component (B) a sulfur-containing antioxidant is a compound represented by the following formula:

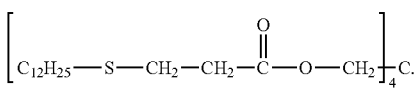

6. The automotive interior/exterior material according to claim 1, wherein the amount of Component (A) and Component (B) are 0.1 to 2.0 parts by mass.

7. The automotive interior/exterior material according to claim 1, wherein the Component (A) a hindered amine compound is a compound represented by the following formula:

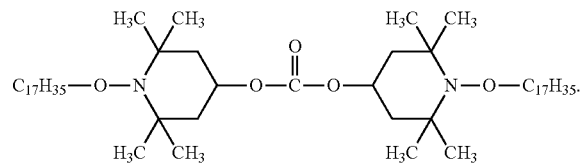

* * * * *